United States Patent
Clarke et al.

(10) Patent No.: US 10,821,062 B2
(45) Date of Patent: *Nov. 3, 2020

(54) COMPOUND FOR USE IN PROTECTING SKIN

(71) Applicants: TDELTAS LIMITED, Thame, Oxfordshire (GB); GOVERNMENT OF THE USA, as represented by THE SECRETARY, DEPARTMENT OF HEALTH & HUMAN SERVICES, Rockville, MD (US)

(72) Inventors: Kieran Clarke, Oxford (GB); Richard Lewis Veech, Rockville, MD (US)

(73) Assignees: TDELTAS LIMITED, Thame (GB); GOVERNMENT OF THE USA, AS REPRESENTED BY THE SECRETARY, DEPARTMENT OF HEALTH AND HUMAN SERVICE, Bethesda, MD (US)

( * ) Notice: Subject to any disclaimer, the term of this patent is extended or adjusted under 35 U.S.C. 154(b) by 83 days.

This patent is subject to a terminal disclaimer.

(21) Appl. No.: 14/774,856

(22) PCT Filed: Sep. 16, 2013

(86) PCT No.: PCT/EP2013/069189
§ 371 (c)(1),
(2) Date: Sep. 11, 2015

(87) PCT Pub. No.: WO2014/139599
PCT Pub. Date: Sep. 18, 2014

(65) Prior Publication Data
US 2016/0030314 A1    Feb. 4, 2016

(30) Foreign Application Priority Data
Mar. 12, 2013 (GB) .................................. 1304467.2

(51) Int. Cl.
*A61Q 17/04* (2006.01)
*A61Q 19/08* (2006.01)
(Continued)

(52) U.S. Cl.
CPC ................. *A61K 8/375* (2013.01); *A61K 8/86* (2013.01); *A61K 9/0014* (2013.01); *A61K 9/06* (2013.01);
(Continued)

(58) Field of Classification Search
CPC ...... A61K 8/375; A61K 31/22; A61K 9/0014; A61K 9/06; A61Q 17/04; A61Q 19/004; A61Q 19/00; A61Q 17/00; A61Q 19/08
See application file for complete search history.

(56) References Cited

U.S. PATENT DOCUMENTS 3,984,566 A   10/1976  Van Scott et al.
4,380,549 A    4/1983  Van Scott et al.
(Continued)

FOREIGN PATENT DOCUMENTS

CA   1330307 C   6/1994
CA   2173270 A   10/1996
(Continued)

OTHER PUBLICATIONS

Supplementary European Search Report and Written Opinion corresponding to European Patent Application No. 09701051.6, dated Jan. 19, 2011.
(Continued)

*Primary Examiner* — Theodore R. West
(74) *Attorney, Agent, or Firm* — Brian C. Trinque; Lathrop GPM LLP

(57) ABSTRACT

A method of protecting animal tissue particularly skin, from damage caused by radiation exposure, by contacting the tissue with a ketone ester, a method of protecting skin,
(Continued)

reducing the deterioration of skin or maintaining or improving the properties of skin by applying topically to the skin a ketone body comprising (R)-3-hydroxybutyrate moieties is disclosed. A ketone body comprising (R)-3-hydroxybutyrate moieties, especially enantiomerically enriched R-1,3-hydroxybutyl-(R)-3-hydroxybutyrate, for such uses is also provided.

9 Claims, 1 Drawing Sheet

(51) Int. Cl.
    *A61K 31/22*     (2006.01)
    *A61K 8/37*     (2006.01)
    *A61Q 19/00*     (2006.01)
    *A61K 9/06*     (2006.01)
    *A61K 9/00*     (2006.01)
    *A61K 47/10*     (2017.01)
    *A61K 31/357*     (2006.01)
    *A61K 8/86*     (2006.01)
    *A61Q 17/00*     (2006.01)

(52) U.S. Cl.
    CPC ............ *A61K 31/22* (2013.01); *A61K 31/357* (2013.01); *A61K 47/10* (2013.01); *A61Q 17/00* (2013.01); *A61Q 17/04* (2013.01); *A61Q 19/00* (2013.01); *A61Q 19/08* (2013.01)

(56) References Cited

U.S. PATENT DOCUMENTS

| | | |
|---|---|---|
| 5,112,865 A | 5/1992 | Nichels et al. |
| 5,281,691 A | 1/1994 | Hubbs et al. |
| 5,468,507 A | 11/1995 | Czap |
| 5,654,266 A | 8/1997 | Chen et al. |
| 5,665,831 A | 9/1997 | Neuenschwander et al. |
| 5,693,850 A | 12/1997 | Birkhahn et al. |
| 6,126,953 A | 10/2000 | Costa et al. |
| 6,136,862 A | 10/2000 | Hiraide et al. |
| 6,207,856 B1 | 3/2001 | Veech |
| 6,268,167 B1 | 7/2001 | Wild et al. |
| 6,316,038 B1 | 11/2001 | Veech |
| 6,323,237 B1 | 11/2001 | Veech |
| 6,380,244 B2 | 4/2002 | Martin et al. |
| 6,544,960 B1 | 4/2003 | Eldred et al. |
| 6,939,570 B1 | 9/2005 | Snow et al. |
| 7,351,736 B2 | 4/2008 | Veech |
| 7,947,736 B2 | 5/2011 | Gross |
| 8,101,653 B2 | 1/2012 | Veech |
| 8,642,654 B2 | 2/2014 | Clarke |
| 9,034,613 B2 | 5/2015 | Robertson et al. |
| 9,211,275 B2 | 12/2015 | Clarke et al. |
| 9,579,302 B2 * | 2/2017 | Veech .................... A61K 31/22 |
| 10,478,415 B2 * | 11/2019 | Veech .................... A61K 31/22 |
| 2001/0014696 A1 | 8/2001 | Veech et al. |
| 2001/0041741 A1 | 11/2001 | Sole et al. |
| 2001/0047008 A1 | 11/2001 | Baraldi |
| 2002/0006959 A1 | 1/2002 | Henderson |
| 2002/0013339 A1 | 1/2002 | Martin et al. |
| 2002/0035231 A1 | 3/2002 | Whitehouse et al. |
| 2003/0022937 A1 | 1/2003 | Veech et al. |
| 2004/0006263 A1 | 1/2004 | Anderson et al. |
| 2004/0063661 A1 | 4/2004 | Linnane |
| 2004/0171671 A1 | 9/2004 | Veech |
| 2004/0266872 A1 | 12/2004 | Veech et al. |
| 2005/0129783 A1 | 6/2005 | McCleary et al. |
| 2005/0165318 A1 | 7/2005 | Brodnick et al. |
| 2005/0181275 A1 | 8/2005 | Jang |
| 2005/0182235 A1 | 8/2005 | Zhong et al. |
| 2006/0078596 A1 | 4/2006 | Clarke et al. |
| 2006/0280721 A1 | 12/2006 | Veech et al. |
| 2007/0179197 A1 | 8/2007 | Henderson et al. |
| 2008/0287372 A1 | 11/2008 | Henderson et al. |
| 2009/0197952 A1 | 8/2009 | Hashim et al. |
| 2009/0253781 A1 | 10/2009 | Veech |
| 2010/0298294 A1 | 11/2010 | Clarke et al. |
| 2011/0237666 A1 | 9/2011 | Clarke et al. |
| 2012/0064611 A1 | 3/2012 | Robertson et al. |
| 2012/0071548 A1 | 3/2012 | Veech |
| 2012/0213835 A1 | 8/2012 | Neas et al. |
| 2013/0102663 A1 | 4/2013 | Clarke et al. |
| 2014/0194509 A1 | 7/2014 | Clarke et al. |
| 2014/0308719 A1 | 10/2014 | Clarke et al. |
| 2015/0065571 A1 | 3/2015 | Clarke et al. |
| 2015/0164855 A1 | 6/2015 | Clarke et al. |
| 2015/0250755 A1 | 9/2015 | Veech et al. |
| 2016/0030314 A1 | 2/2016 | Clarke et al. |
| 2016/0193173 A1 | 7/2016 | Clarke et al. |

FOREIGN PATENT DOCUMENTS

| | | |
|---|---|---|
| CN | 1483355 A | 9/2002 |
| CN | 1552315 A | 12/2004 |
| DE | 20205184 U | 12/2002 |
| EP | 0 266 217 A2 | 5/1988 |
| EP | 0 537 113 A1 | 4/1993 |
| EP | 0552896 A1 | 7/1993 |
| EP | 0 721 740 A1 | 7/1996 |
| EP | 1568780 A1 | 8/2005 |
| EP | 1809235 B1 | 7/2007 |
| EP | 2 875 812 A1 | 5/2015 |
| GB | 1524611 A | 9/1978 |
| GB | 0312603.4 | 6/2003 |
| GB | 0313760.1 | 6/2003 |
| GB | 2511941 A | 9/2014 |
| JP | S54-138126 A | 10/1979 |
| JP | S5747446 A | 3/1982 |
| JP | S63-112998 A | 5/1988 |
| JP | H01-095730 A | 4/1989 |
| JP | H01-160917 A | 6/1989 |
| JP | H03-083950 A | 4/1991 |
| JP | H04-112825 A | 4/1992 |
| JP | H07-076513 A | 3/1995 |
| JP | H08-191664 A | 7/1996 |
| JP | H10-175855 A | 6/1998 |
| JP | H10-265378 A | 10/1998 |
| JP | H10-313819 A | 12/1998 |
| JP | 2001-515510 A | 9/2001 |
| JP | 2005247821 A | 9/2005 |
| JP | 2008-513017 A | 5/2008 |
| JP | 2008127369 A | 6/2008 |
| JP | 2008-263825 A | 11/2008 |
| JP | 2009532496 A | 9/2009 |
| JP | 2012500264 A | 1/2012 |
| JP | 2016512207 A | 4/2016 |
| SU | 507322 A | 3/1976 |
| WO | 1987003806 A1 | 7/1987 |
| WO | 1995009144 A1 | 4/1995 |
| WO | 1998/041201 A1 | 9/1998 |
| WO | 1998041200 A1 | 9/1998 |
| WO | 1999/024451 A2 | 5/1999 |
| WO | 2000004895 A1 | 2/2000 |
| WO | 2000015216 A1 | 3/2000 |
| WO | 2001013877 A1 | 3/2001 |
| WO | 2001051645 A1 | 7/2001 |
| WO | 2002/006835 A1 | 1/2002 |
| WO | 2003/012417 A2 | 2/2003 |
| WO | 2003/056319 A2 | 7/2003 |
| WO | 2003/097860 A1 | 11/2003 |
| WO | 2004105742 A1 | 12/2004 |
| WO | 2004108740 A1 | 12/2004 |
| WO | 2006020137 A2 | 2/2006 |
| WO | 2006/031941 A2 | 3/2006 |
| WO | 2006/061624 A1 | 6/2006 |
| WO | 2006070337 A2 | 7/2006 |
| WO | 2007001883 A2 | 1/2007 |
| WO | 2007063037 A1 | 6/2007 |
| WO | 2007115282 A2 | 10/2007 |
| WO | 2007115934 A1 | 10/2007 |
| WO | 2008/074473 A2 | 6/2008 |
| WO | 2008119032 A1 | 10/2008 |

(56) References Cited

FOREIGN PATENT DOCUMENTS

| | | |
|---|---|---|
| WO | 2008140828 A1 | 11/2008 |
| WO | 2009023357 A2 | 2/2009 |
| WO | 2009/045481 A1 | 4/2009 |
| WO | 2009/089144 A1 | 7/2009 |
| WO | 2010021766 A1 | 2/2010 |
| WO | 2010120300 A1 | 10/2010 |
| WO | 2011101171 A1 | 8/2011 |
| WO | 2011121540 A1 | 10/2011 |
| WO | 2012113415 A1 | 8/2012 |
| WO | 2013/150153 A1 | 10/2013 |
| WO | 2014071389 A1 | 5/2014 |
| WO | 2014/153416 A1 | 9/2014 |
| WO | 2014139599 A1 | 9/2014 |

OTHER PUBLICATIONS

Search Report corresponding to Great Britain Patent Application No. 1002983.3, dated Jun. 10, 2010.

International Preliminary Report on Patentability corresponding to International Patent Application No. PCT/EP2013/069189, dated Sep. 15, 2015.

Larios et al. (2004) "Synthesis of flavor and fragrance esters using Candida antarctica lipase," Appl. Microbiol. Biotechnol. 65:373-376.

U.S. Appl. No. 13/580,602 US 2013-0102663 A1, filed Jan. 4, 2013 Apr. 25, 2013, Kieran Clarke.

U.S. Appl. No. 11/287,803 US 2006-0078596 A1, filed Nov. 28, 2005 Apr. 13, 2006, Kieran Clarke.

U.S. Appl. No. 10/559,258 US 2006-0280721 A1, filed Jun. 8, 2006 Dec, 14, 2006, Richard L Veech.

U.S. Appl. No. 12/811,648 US 2010-0298294 A1, filed Jul. 2, 2010 Nov. 25, 2010, Kieran Clarke.

U.S. Appl. No. 14/931,265, filed Nov. 3, 2015, Kieran Clarke.

U.S. Appl. No. 13/264,533 US 2012-0064611 A1 U.S. Pat. No. 9,034,613, filed Oct. 14, 2011 Mar. 15, 2012 May 19, 2015, Jeremy Robertson.

U.S. Appl. No. 14/213,713 US 2014-0308719 A1, filed Mar. 14, 2014 Oct. 16, 2014, Kieran Clarke.

U.S. Appl. No. 14/453,999 US 2015-0065571 A1, filed Aug. 7, 2014 Mar. 5, 2015, Kieran Clarke.

U.S. Appl. No. 14/390,495 US 2015-0164855 A1, filed Oct. 3, 2014 Jun. 18, 2015, Kieran Clarke.

U.S. Appl. No. 14/440,634 US 2015-0250755 A1, filed May 5, 2015 Sep. 10, 2015, Richard L. Veech.

U.S. Appl. No. 14/774,856, filed Sep. 11, 2015, Kieran Clarke.

U.S. Appl. No. 13/031,006 US 2011-0237666 A1 U.S. Pat. No. 8,642,654, filed Feb. 18, 2011 Sep. 29, 2011 Feb. 4, 2014, Kieran Clarke.

U.S. Appl. No. 14/101,834 US 2014-0194509 A1, filed Dec. 10, 2013 Jul. 10, 2014, Kieran Clarke.

Abdelwahab et al. (2012) "The Ketogenic Diet Is an Effective Adjuvant to Radiation Therapy for the Treatment of Malignant Glioma," PLOS ONE. 7(5):E36197. pp. 1-7.

Boyarinov et al. (1984) "Effect of Sodium hydroxybutyrate on myocardial high-energy phosphates, function, and ultrastructure after blood loss", Biulleten' eksperimental'noT biologii i meditsiny. 97(3):289-292.

Buteau (2009) "Obviousness of Enantiomers over Prior Art Racemates," The Journal of High Technology Law. L22. pp. 42-49.

Clark et al. (2005) "Dilated Cardiomyopathy and Acute Liver Injury Associated with Combined Use of Ephedra, γ-Hydroxybutyrate, and Anabolic Steroids" Pharmacotherapy. 25(5):756-761.

Davey et al. (1988) "Radioprotection of rat subependymal plate with 4-0H sodium butyrate," NCI Monogr. (6):231-234.

Desrochers et al. (1995) "Metabolism of {R,S)-1 ,3-butanediol acetoacetate esters, potential parenteral and enteral nutrients in conscious pigs," Am. J. Physiol. 268:E660-667.

Desrochers et al. (1995) "R, 5-1, 3-butanediol acetoacetate esters, potential alternates to lipid emulsions for total parenteral nutrition," Journal of Nutritional Biochemistry. 6(2):111-118.

Desrochers et al. (1992) "Metabolism of R and S-1 ,3-butanediol in perfused livers from meal-fed and starved rats," Biochem. J. 285:647-653.

Eagles et al. (1997) "The effects of combined treatment with 131-selective receptor antagonists and lipid-lowering drugs on fat metabolism and measures of fatigue during moderate intensity exercise: a placebo-controlled study in healthy subjects," Brit. J. Clinical Pharmacol. 43:291-300.

Edegger et al. (2006) "Regia- and Stereoselective Reduction of Diketones and Oxidation of Dials by Biocatalytic Hydrogen Transfer," Eur. J. Org. Chem. 2006(8):1904-1909.

Felig et al. (1971) "Amino acid metabolism in exercising man." J. Clin. Invest. 50(12):2703-2714.

Goldbort et al. (1976) "Butanediols: Selection, open field activity, and NAD reduction by liver extracts in inbred mouse strains," Pharmacology Biochemistry and Behaviour. 5(3):263-268.

Kalaitzakis et al. (2005) "Highly Stereoselective Reductions of a-Aikyl-1 ,3-diketones and a-Aikyi-Jl-keto Esters Catalyzed by Isolated NADPH-Dependent Ketoreductases," Org. Lett. 7(22):4799-4801.

Kashiwaya et al. (2013) "A ketone ester diet exhibits anxiolytic and cognition-sparing properties, and lessens amyloid and tau pathologies in a mouse model of Alzheimer's disease," Neurobiology of Aging. 34(6):1530-1539.

Kohut et al. (1995) "Effects of decresased free fatty acids on fatigue during exercise with carbohydrate feedings," Medicine and Science in Sports & Exercise. 27(5 Suppi):S102.

Kulinskii et al. (1993) "The radioprotective effect of GABA-tropic substances, gamma-hydroxybutyrate and piracetam," Radiobiologiia. 33(1):133-136.—English Abstract Only.

Mori et al. (1987) "New synthesis of both enantiomers of grandisol, the boll weevil pheromon," Tetrahedron. 43 (10):2229-2239.

Nair et al. (1988) "Effect of beta-hydroxybutyrate on whole-body leucine kinetics and fractional mixed skeletal muscle protein synthesis in humans," J. Clin. Invest. 82(1 ):198-205.

Neubauer et al. (1997) "Myocardial Phosphocreatine-to-ATP Ratio is a predictor of mortality in patients with dilated cardiomyopathy," Circulation. 96:2190-2196.

Ostrovskaya et al. (1981) "Effect of prolonged administration of sodium hydroxybutyrate on the working capacity and muscle tissue in rats," Farmakologiya I Toksikologiya. 44(5):534-539.—Only English Abstract Provided.

Puchowicz et al. (2000) "Dog model of therapeutic ketosis induced by oral administration of R,S-1 ,3-butanediol diacetoacetate," J. Nutr. Biochem. 11:281-287.

Rossi et al. (2000) "Suppression of Feed Intake after Parenteral Administration of D-β β-Hydroxybutyrate in Pygmy Goats," J. Vet. Med. A. 47:9-16.

Shaw et al. (1984) "Influence of beta-hydroxybutyrate infusion on glucose and free fatty acid metabolism in docs," Am. J. Phys. 247:E756-764.

Sherwin et al. (1975) "Effect of ketone infusions on amino acid and nitrogen metabolism in man" J. Clin. Invest. 55(6) 1382-1390.

Simons et al. ( 1982) "Long term treatment with Slow Release Oxprenolol Alone, or in Combination with other Drugs: Effects on Blood Pressure, Lipoproteins and Exercise Performance," Aust. N. Z. J. Med. 12:612-616.

Smith et al. (1975) "Initial effect of injury on ketone bodies and other blood metabolites," Lancet. 1(7897):1-3.

Tobin et al., "Effect Of 1 ,3-Butanediol and Propionic Acid on Blood Ketones, lipids d Metal Ions in Rats", Journal of Nutrition, vol. 102, No. 8, 1972, pp. 1001-1008.

Turner et al. "Glycemic control with diet, sulfonylurea, metformin, or insulin in patients with type 2 diabetes mellitus: progressive requirement for multiple therapies (UKPDS 49)." Jama 281.21 (1999): 2005-2012.

Wu et al. (1987) "Ketone bodies inhibit leucine degradationin chick skeletal muscle," International J. of Biochem. 19 ( 10 ):937-943.

(56) References Cited

OTHER PUBLICATIONS

Zhu et al. (2006) "A recombinant ketoreductase tool-box. Assessing the substrate selectivity and stereoselectivity toward the reduction of Jl-ketoesters," Tetrahedron. 62:901-905.

"Drug Therapy of Dyslipidemia" in Goodman & Gilman's The Pharmacological Basis of Therapeutics, 11th Ed., McGraw-Hill (New York), pp. 948-953 (2006).

International Search Report with Written Opinion corresponding to International Patent Application No. PCT/EP2014/067027, dated Oct. 30, 2014.

International Search Report corresponding to International Patent Application No. PCT/EP2014/055158, dated Jun. 25, 2014.

International Search Report with Written Opinion corresponding to International Patent Application No. PCT/US2013/068545, dated Jan. 20, 2014.

International Search Report with Written Opinion corresponding to International Patent Application No. PCT/EP2013/069189, dated Aug. 12, 2014.

International Search Report with Written Opinion corresponding to International Patent Application No. PCT/EP2013/057250, dated Jun. 11, 2013.

International Search Report with Written Opinion corresponding to International Patent Application No. PCT/EP2011/000833, dated Jun. 22, 2011.

International Preliminary Report on Patentability corresponding to International Patent Application No. PCT/US2009/040773, dated Oct. 18, 2011.

International Search Report with Written Opinion corresponding to International Patent Application No. PCT/US2009/040773, dated Feb. 22, 2010.

International Search Report with Written Opinion corresponding to International Patent Application No. PCT/US2009/040766, dated Aug. 6, 2009.

International Preliminary Report on Patentability for International Application No. PCT/US2009/030095 dated Jul. 6, 2010.

International Search Report for for International Application No. PCT/US2009/030095 dated Feb. 23, 2009.

International Search Report with Written Opinion corresponding to International Patent Application No. PCT/US2004/018016, dated Apr. 15, 2005.

International Search Report with Written Opinion corresponding to International Patent Application No. PCT/GB2004/002286, dated Oct. 11, 2004.

Search and Examination Report corresponding to Great Britain Patent Application No. 1414016.4, dated Aug. 29, 2014.

Search and Examination Report corresponding to Great Britain Patent Application No. 1404577.7, dated Oct. 23, 2014.

Search and Examination Report corresponding to Great Britain Patent Application No. 1404400.2, dated Mar. 26, 2014.

Examination Report corresponding to Great Britain Patent Application No. 1404400.2, dated Aug. 18, 2014.

Search Report corresponding to Great Britain Patent Application No. 1314127.0. dated Jan. 31, 2014.

Search Report corresponding to Great Britain Patent Application No. 1304467.2, dated Aug. 23, 2013.

Clarke et al. (2012) "Oral 28-day and developmental toxicity studies of (R)-3-hydroxybutyl (R)-3-hydroxybutyrate," Regulatory Toxicology & Pharmacology. 63(2)196-208.

Laffel (1999) "Ketone bodies: a review of physiology, pathophysiology and application of monitoring to diabetes," Diabetes Metabol. Res. Rev. 15(6):412-426.

Leckey et al. (Oct. 2017) "Ketone Diester Ingestion Impairs Time-Trial Performance in Professional Cyclists," Front Physiol. 8:806.

Ley (2008) "Masking Bitter Taste by Molecules," Chem. Percept. 1:58-77.

Lunde et al. (1998) "Skeletal muscle fatigue in normal subjects and heart failure patients. Is there a common mechanism?" Acta Physiol. Scand. 162:215-228.

Ojeda et al. (1977) "[Radiation response of mitochondria in dependence on their metabolic status (author's transl)]" Strahlentherapie. 153(2):117-123.

Suzuki et al. (1986) "Acetylputrescine deacetylase from Micrococcus luteus K-11," Biochimica et Biophysica Acta. 882:140-142.

Westerblad et al. (2002) "Recent advances in the understanding of skeletal muscle fatigue," Curr. Opin. Rheumatol. 14:648-652.

Wilson (1996) "Evaluation of Skeletal Muscle Fatigue in Patients with Heart Failure," J. Mol. Cell/ Cardiol. 28:2287-2292.

Chen et al. (Feb. 2016) "Beta-hydroxybutyrate reduces alcoholic steatohepatits (ASH) via activation of the GPR 109A Receptor," Proceedings of the American Society for Hematology, 2016. Abstract No. 26. pp. 143-144.

Farmer et al. (1973) "Radioprotective Thiazolidines from beta-keto esters," J. Med. Chem. 16(4):411-413.

Baron et al. (1991) "Mechanism of insulin resistance in insulin-dependent diabetes mellitus: a major role for reduced skeletal muscle blood flow," J. Clin. Endocrinol. Metab. 73(3):637-643.

Boehm et al. (2001) "Increased uncoupling proteins and decreased efficiency in the palmitate-perfused hyperthyroid rat heart," Am. J. Physiol. Heart Circ. Physiol. 2809(3):H977-H983.

Casey et al. (1990) In; Advanced Practical Organic Chemistry. Blackie. Glasgow and London, U.K. pp. 158-160.

Chatham et al. (1999) "Preferential inhibition of lactate oxidation relative to glucose oxidation in the rat heart following diabetes," Cardiovasc Res. 43(1):96-106.

Chatham et al. (2002) "Cardiac carbohydrate metabolism in Zucker diabetic fatty rats," Cardiovasc Res. 55(1):104-112.

Chen et al. (Nov. 13, 2016) "β-hydroxybutyrate protects from alcoholic hepatitis via a GPR109a-C/EBPβ dependent pathway," AASLD LiverLearning. Abstract No. 1629. Accessible on the Internet at URL: http://liverlearning.aasld.org/aasld/2016/thelivermeeting/144521/yonglin.chen.b-hydroxybutyrate.protects.from.alcoholic.hepatitis.via.a.html. [Last Accessed Apr. 5, 2017].

Cole et al. (2011) "A high fat diet increases mitochondrial fatty acid oxidation and uncoupling to decrease efficiency in rat heart," Basic Res. Cardiol. 106:447-457.

Cox et al. (Oct. 29, 2014) "Acute nutritional ketosis: implications for exercise performance and metabolism," Extrem. Physiol Med. 3:17. pp. 1-9.

Demir et al. (2001) "Serum HbA1c levels and exercise capacity in diabetic patients," Jpn. Heart J. 42(5):607-616.

Estacio et al. (1998) "The association between diabetic complications and exercise capacity in NIDDM patients," Diabetes Care. 21(2):291-295.

Frayn (2003) In; Metabolic Regulation: A Human Perspective. 2nd Ed. Blackwell Science. pp. 94-96.

Gangemi "Enhancing Athletic Performance by Predicting Fatigue and Preventing Muscle Failure," Accessible on the Internet at URL: http://www.drgangemi.com/wp-content/uploads/2011/01/GANGEMI-PREDICTING-FATIGUE-AND-MUSCLE-FAILURE.pdf. [Last Accessed Sep. 20, 2011].

Iozzo et al. (2002) "Mismatch between insulin-mediated glucose uptake and blood flow in the heart of patients with Type II diabetes," Diabetologia. 45(10):1404-1409.

Kemper et al. (Oct. 26, 2015) "An Ester of β-Hydroxybutyrate Regulates Cholesterol Biosynthesis in Rats and a Cholesterol Biomarker in Human," Lipids. 50(12):1185-1193.

Knowler et al. (2002) "Reduction in the incidence of type 2 diabetes with lifestyle intervention or metformin," New Engl. J. Med. 346:393-403.

Komiyama et al. (2000) "Near-infrared spectroscopy grades the severity of intermittent claudication in diabetes more accurately than ankle pressure measurement," British Journal of Surgery. 87(4):459-466.

Komiyama et al. (2004) "Effects of a 4-week 70% high carbohydrate / 15% low fat diet on glucose tolerance and on lipid profiles," Diabetes Res. Clin. Pract. 64(1):11-18.

Kwiterovich et al. (2003) "Effect of a high-fat ketogenic diet on plasma levels of lipids, lipoproteins, and apolipoproteins in children," JAMA. 290(7):912-920.

(56) References Cited

OTHER PUBLICATIONS

Lanni et al. (2002) "De Novo Expression of Uncoupling Protein 3 is Associated to Enhanced Mitochondrial Thioesterase-1 Expression and Fatty Acid Metabolism in Liver of Fenofibrate-treated Rats," FEBS Letters. 525:7-12.

Libby et al. (2002) "Diabetic macrovascular disease. The glucose paradox?" Circulation. 106(22):2760-2763.

Lodi et al. (1999) "Reduced cytosolic acidification during exercise suggests defective glycolytic activity in skeletal muscle of patients with Becker muscular dystrophy. An in vivo 31P magnetic resonance spectroscopy study," Brain. 121(1):121-130.

Madsen et al. (1999) "Near-infrared oximetry of the brain," Prog. Neurobiol. 58(6):541-560.

Mahler et al. (1999) "Type 2 diabetes mellitus: update on diagnosis, pathophysiology, and treatment," J. Clin. Endocrinol. Metab. 84(4)1165-1171.

Meyer et al. (1997) "Myocardial blood flow and glucose metabolism in diabetes mellitus," Am. J. Cardiol. 80(3,Suppl 1):94A-101A.

Mori et al. (1984) "Synthesis of the Propionates of (2R, 8R)- and (2S, 8R)-8-methyl-2-decanol, the pheromone of the Western corn rootworm, employing chiral compounds of microbial origin as starting material," Tetrahedron. 40(2):299-303.

Murray et al. (2004) "Uncoupling Proteins in Human Heart," Lancet. 364:1786-1788.

Murray et al. (2005) "Plasma Free Fatty Acids and Peroxisome Proliferator-Activated Receptor a in the Control of Myocardial Uncoupling Protein Levels," Diabetes. 54(12):3496-3502.

Newsholme et al. (1986) In; Biochemistry for the Medical Sciences. John Wiley & Sons. Chichester, U.K. pp. 324-331.

O'Neill et al. (1994) "A simple enantioselective synthesis of γ-valerolactone," Tetrahedron Asymmetry. 5(1):117-118.

Paolisso et al. (1999) "Prognostic importance of insulin-mediated glucose uptake in aged patients with congestive heart failure secondary to mitral and/or aortic valve disease," Am. J. Cardiol. 83(9):1338-1344.

Perez-Jimenez et al. (2001) "A Mediterranean and a high-carbohydrate diet improve glucose metabolism in healthy young persons," Diabetologia. 44(11):2038-2043.

Richieri et al. (1995) "Unbound free fatty acid levels in human serum," Journal of Lipid Research. 36(2):229-240.

Rodrigues et al. (1998) "Metabolic disturbances in diabetic cardiomyopathy," Molecular and Cellular Biochemistry. 180(1-2):53-57.

Salehizadeh et al. (2004) "Production of polyhydroxyalkanoates by mixed culture: recent trends and biotechnological importance," Biotechnol. Advances. 22:261-279.

Sato et al. (1995) "Insulin, ketone bodies, and mitochondria! energy transduction," FASEB J. 9(8):651-658.

Scheuermann-Freestone et al. (2003) "Abnormal cardiac and skeletal muscle energy metabolism in patients with type 2 diabetes," Circulation. 107(24):3040-3046.

Seebach et al. (1993) "Direct Degradation of the Biopolymer Poly[(R)-3-Hydroxybutyric Acid] to (R)-3-Hydroxybutanoic Acid and its Methyl Ester," Organic Syntheses, Coll. vol. 9., p. 483 (1998); vol. 71., p. 39. (1993).

Sidell et al. (2002) "Thiazolidinedione treatment normalizes insulin resistance and ischemic injury in the Zucker fatty rat heart," Diabetes. 51(4):1110-1117.

Silva et al. (2004) "Poly-3-hydroxybutyrate (P3HB) production by bacteria from xylose, glucose and sugarcane bagasse hydrolysate," J. Ind. Microbiol. Biotechnol. 31:245-254.

Smith et al. (2002) "Magnetic Resonance Spectroscopy in Medicine: Clinical Impact," Progress in Nuclear Magnetic Resonance Spectroscopy. 40:1-34.

Stanley et al. (1997) "Regulation of energy substrate metabolism in the diabetic heart," Cardiovasc. Res. 34 (1):25-33.

Taegtmeyer et al. (2002) "Adaptation and maladaptation of the heart in diabetes: Part I. General concepts," Circulation. 105(14):1727-1733.

Tinnikov et al. (1999) "Colorimetric micro-determination of free fatty acids in plasma using microplate readers," Clinica Chemica Acta. 281(1-2):159-162.

Toubro et al. (1998) "Twenty-four-hour respiratory quotient: the role of diet and familial resemblance," J. Clin. Endocrinol. Metabol. 83(8):2758-2764.

Tunaru et al. (2003) "PUMA-G and HM74 are receptors for nicotinic acid and mediate its anti-lipolytic effect," Nat. Med. 9(3):352-355.

Zange et al. (2002) "Creatine Supplementation Results in Elevated Phosphocreatine/Adenosine Triphosphate (ATP) Ratios in the Calf Muscle of Athletes But Not in Patients with Myopathies," Annals of Neurology. 53(1)126-127.

International Search Report with Written Opinion corresponding to International Patent Application No. PCT/EP2014/055158, dated Jun. 25, 2014.

International Search Report with Written Opinion corresponding to International Patent Application No. PCT/US2009/030095, dated Feb. 23, 2009.

* cited by examiner

COMPOUND FOR USE IN PROTECTING SKIN

RELATED APPLICATIONS

This application is a 35 U.S.C. § 371 filing of International Application No. PCT/EP2013/069189, filed Sep. 16, 2013, which claims priority to Great Britain Patent Application No. 1304467.2, filed Mar. 12, 2013, each of which are incorporated herein by reference in their entireties.

This invention relates to a compound for use in protecting skin, a method for preventing or reducing the risk of damage to skin and a composition for topical use to protect skin, to reduce the deterioration of skin due to ageing or due to the harmful effects of radiation or to maintain or to improve its properties. In particular, the invention relates to a ketone monoester for such uses and to a topical composition comprising the ketone ester.

It is known that radiation damages biological tissues and cells, for example skin. Treatment of skin to reduce the harmful effects of radiation, particularly ultra violet (UV) radiation, or deterioration due to ageing is well known.

Reducing the rate of deterioration or maintaining or improving skin properties, for example the appearance and feel of skin, has received a great deal of research effort and topical compositions for treating skin have been known since the earliest times. Dry skin also presents problems for many people. Personal care products such as skin creams and lotions, shampoos, conditioners, toilette bars, shower gels and antiperspirant and deodorants are typically normally formulated with at least one material to address dry skin. Symptoms such as itching, flaking and a visually displeasing dermal appearance can all to some extent be ameliorated. A wide range of products have been developed to address these problems and include occlusives such as petrolatum or silicone oils which serve to inhibit loss of natural moisture. Occlusives form a barrier between the epidermis and the environment. Keratolytic agents have also been employed to enhance rate of dermal exfoliation. Alpha-hydroxy acids are the most common agents for achieving exfoliation. A further approach is in the topical application of humectants and hydroxylated monomeric and polymeric organic substances are typically used for this purpose. Glycerin (glycerol) is well known for this use. Conventional topical applications typically deal primarily with the dead surface layers of the skin and may provide benefits upon application by the user, providing the user with a positive experience of ameliorating a skin condition or the effect of ageing.

It is also known to treat skin using ingestible ingredients to provide improvements in skin appearance and texture. These ingredients act by accessing the living interior of the skin. Examples of ingestible ingredients for treating skin include dietary fish oil and carotenoids such as lycopene and β-carotene which are known to offer protection against UVR-induced erythema upon ingestion. Vitamins E & C when taken orally in combination have also been shown to provide protection against UVR-induced erythema. Ingestible treatments may be perceived as providing a medical effect and may not provide the user with an immediate sense of improvement as compared to topical compositions.

There remains a need for compositions that can provide beneficial effects on skin including one or more of providing hydration, an anti-ageing effect, improved visual dermal appearance, reduced dryness, treating sunburn and the like and treating medical conditions for example eczema and psoriasis or other problems described above.

Ketone bodies and ketone body esters are known to reduce the levels of free fatty acids circulating in the plasma of a subject for example as disclosed in WO2004/105742 and ingestion of ketone bodies may lead to various clinical benefits. They are known for a treating a range of medical conditions including an enhancement of cognitive performance, treatment of cardiovascular conditions, diabetes and treatment of mitochondrial dysfunction disorders and in treating muscle fatigue and impairment and are also known to provide advantageous effects as a food product, nutritional supplement or supplement or as a nutraceutical for example in rehydration.

WO2004/108740 discloses a wide range of compounds and compositions containing (R)-3-hydroxybutyrate derivatives, with emphasis on oligomers of hydroxybutyrates, effective for elevating blood concentrations of ketone bodies. Ketone bodies are produced when fatty acids levels are raised in the body and are metabolised by the body for energy. In known applications, ketone bodies have been administered enterally or parenterally to a subject.

A wide range of ketone bodies containing R-3-hydroxybutyrate are known including oligomers, esters of oligomers, salts, the acid form, esters of the acid with mono, di or trihydric alcohols, However ketone bodies have not to date been employed topically for preventing or reducing the risk of damage to skin, to protect skin, to reduce the deterioration of skin due to ageing or due to the harmful effects of radiation or to maintain or to improve its properties.

Dermal fibroblasts are responsible for generating connective tissue and allowing the skin to recover from injury. Human dermal fibroblasts (HDF) in culture rely primarily upon glucose to fuel both aerobic and anaerobic metabolism. We have now found that a specific ketone body provides beneficial effects on skin and protects dermal fibroblasts from radiation, particularly UV radiation when applied topically. The ketone may also provides beneficial effects upon topical application to gums and soft tissue. The user may also experience positive psychological effects associated with the improved properties being the result of the process of the user themselves applying the ketone ester topically.

Figure 1:
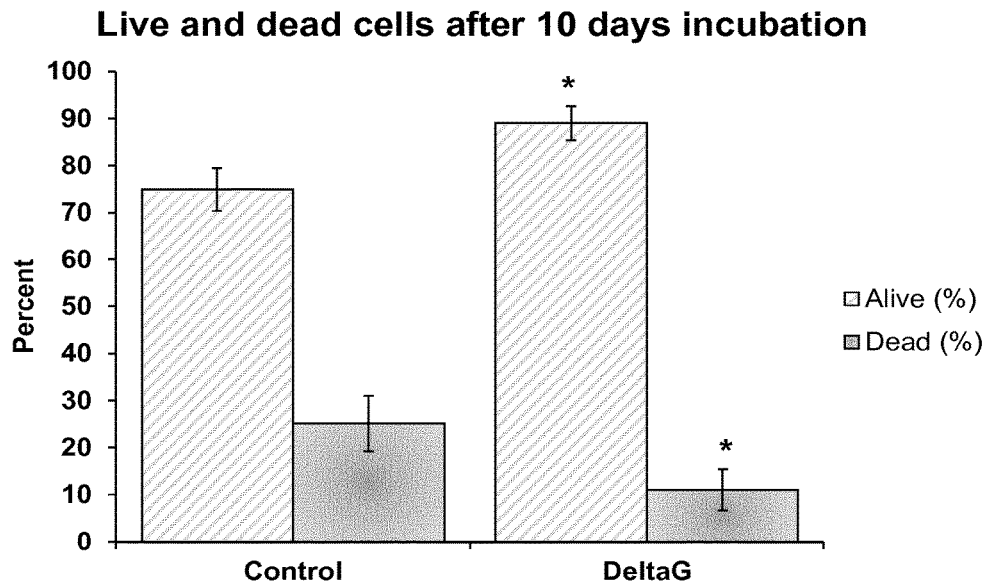
FIG. 1 is a graph depicting the percentage of live and dead human dermal fibroblasts following an incubation period under control conditions or in the presence of R-3-hydroxybutyl-(R)-3-hydroxybutyrate.

DETAILED DESCRIPTION OF THE INVENTION:

The invention provides in a first aspect a ketone body comprising (R)-3-hydroxybutyrate moieties for topical use in protecting skin, reducing the deterioration of skin or maintaining or improving the properties of skin.

The invention provides in a second aspect a ketone body comprising (R)-3-hydroxybutyrate moieties for use in a method for protecting skin, reducing the deterioration of skin or maintaining or improving the properties of skin which comprises applying topically to the skin the said ketone body.

In a further aspect, the invention provides a method of protecting skin, reducing the deterioration of skin or maintaining or improving the properties of skin comprising applying topically to the skin a ketone body comprising (R)-3-hydroxybutyrate moieties.

The invention also provides in a further aspect for use a ketone body comprising (R)-3-hydroxybutyrate moieties as a topical agent for protecting skin, reducing the deterioration of skin or maintaining or improving the properties of skin.

Skin may deteriorate for many reasons including ageing or due to the harmful effects of radiation. The ketone ester of the invention may reduce the rate of such deterioration. The ketone ester comprising (R)-3-hydroxybutyrate moieties is especially beneficial in protecting human dermal fibroblasts from radiation, for example UV-B radiation. The ketone body may be applied at any time to the skin, before, during or after exposure to radiation.

Properties of skin which may be maintained or improved include one or more of providing hydration, an anti-ageing effect, improved visual dermal appearance, reduced dryness, treating sunburn and the like and treating medical conditions for example eczema and psoriasis.

In a further aspect, the invention provides a topical composition comprising (R)-3-hydroxybutyrate moieties and an excipient for topical application. The composition is suitable for topical use in one or more of protecting skin, reducing the deterioration of skin due to ageing or due to the harmful effects of radiation and maintaining or improving properties of skin.

Preferably, the excipient comprises a cosmetically acceptable carrier.

The invention also provides a method for improving skin properties comprising topically applying to the skin a composition according to the invention.

In a further aspect, the invention provides a method of treatment of skin comprising applying a composition to the skin, the composition comprising (R)-3-hydroxybutyrate moieties and an excipient for topical application to aid spreading across the skin or absorption into the skin of the (R)-3-hydroxybutyrate moieties.

Advantageously, the ketone body and composition according to the invention provides beneficial effects on skin properties upon topical application and a desirable user experience. Suitably, the composition is readily spreadable over skin and absorbable into skin but preferably does not pass through skin.

The ketone body and composition of the invention may also beneficially be applied topically to the gums or soft tissue to protect the same.

Without wishing to be bound by any theory, it is believed that the ketone bodies in the composition are metabolised to produce ATP for energy and nourishment to cells. Conventional skin treatments applied topically employ fats or the like to provide a physical effect or to prevent water evaporating, so retaining moisture in the dermis. Further, it is believed that conventional topical compositions for improving skin properties act in a physical way utilising bulk properties of the composition, for example by applying oils or retaining moisture. However the inventor has found that by employing the ketone ester which acts at a cellular level and applying the ester topically provides a combination of desirable user experience and improvement in skin properties.

The invention also provides a method of achieving an anti-ageing effect in the skin of a human or non-human mammal (preferably a human), which comprises applying to the skin of the human or non-human mammal an amount of a ketone body or a composition according to the invention which is effective to achieve said anti-ageing effect.

As used herein, the term "ketone", "ketone body" or "ketone bodies" means a compound or species which is a ketone or a ketone body precursor, that is, a compound or species which is a precursor to a ketone and which may be converted or metabolised to a ketone. In a preferred embodiment the ketone body comprises a ketone body ester or a partial ester of a ketone body.

Any ketone body or ketone body ester containing (R)-3-hydroxybutyrate moieties may be employed in the invention. Preferably, the ketone body comprises a ketone monoester. Examples of suitable ketone bodies or compounds which provide (R)-3-hydroxybutyrate moieties in situ include oligomers of hydroxybutyrates, triolide, acetoacetate and esters thereof and any precursors of beta hydroxybutyrate which are metabolisable in skin cells.

We have surprisingly found that R-3-hydroxybutyl-(R)-3-hydroxybutyrate, a ketone monoester are metabolised more effectively than other forms of hydroxybutyrate, particularly oligomers.

According to a further aspect of the invention, there is provided a ketone body comprising R-3-hydroxybutyl-(R)-3-hydroxybutyrate for topical use in protecting skin reducing the deterioration of skin or maintaining or improving the properties of skin.

Preferably, the ketone body comprises enantiomerically enriched R-1,3-hydroxybutyl-(R)-3-hydroxybutyrate. R-1,3-hydroxybutyl-(R)-3-hydroxybutyrate monoester may be employed in combination with other ketone bodies or ketone body precursors, for example acetoacetate. The R-1,3-hydroxybutyl-(R)-3-hydroxybutyrate monoester may be present in an amount less than any other such ketone bodies but preferably is present in an amount more than any such other ketone body. In an especially preferred embodiment R-1,3-hydroxybutyl-(R)-3-hydroxybutyrate monoester is the only ketone body or ketone body precursor present in the composition of the invention.

The level of ketone body or a ketone body ester in the composition suitably comprises at least 1% by weight of ketone body more preferably at least 10% by weight and up to 95% by weight of the composition. Whilst a level of 15 to 30% by weight of the composition may be suitable, a composition comprising from 30 to 95%, especially 50 to 95% by weight of the composition may be preferred depending on the skin condition being treated.

A composition of the invention may further comprise a medium chain triglyceride (MCT) and, optionally, their associated fatty acids. MCTs comprise fatty acids with a chain length of between 5 and 12 carbon atoms. It is known that a diet rich in MCT increases blood ketone levels. Suitable medium chain triglycerides are represented by the following formula $CH_2R_1$—$CH_2R_2$—$CH_2R_3$ wherein R1, R2 and R3 are fatty acids having 5 to 12 carbon atoms. Preferably, MCTs wherein R1, R2, and R3 are fatty acids containing a six-carbon backbone (tri-C6:0) are employed.

Where an MCT is employed, suitably the composition of the invention comprises i) a ketone body, preferably a ketone monoester, more preferably a D-β-hydroxybutyrate monoester, ii) a MCT, preferably tri-C6:0 MCT and iii) a cosmetically acceptable carrier.

The composition of the invention may also comprise L-carnitine or a derivative of L-carnitine. Examples of derivatives of L-carnitine include decanoylcarnitine, hexanoylcarnitine, caproylcarnitine, lauroylcarnitine, octanoylcarnitine, stearoylcarnitine, myristoylcarnitine, acetyl-L-carnitine, O-Acetyl-L-carnitine, and palmitoyl-L- carnitine. Where a carnitine is employed, suitably the composition of the invention comprises i) a ketone body, preferably a ketone monoester, more preferably a D-β-hydroxybutyrate monoester and ii) L-carnitine or a derivative of L-carnitine.

Where MCT and L-carnitine or its derivative is employed, suitably the MCT is emulsified with the carnitine. Preferably 10 to 500 g of emulsified MCT is combined with 10 to 2000 mg of carnitine for example 50 g MCT (95% triC8:0) emulsified with 50 g of mono- and di-glycerides combined with 500 mg of L-carnitine.

The MCT may be present in a greater amount than the ketone body but preferably the level of ketone body is greater than the level of the MCT.

The composition may be in solid form or in liquid form for example a suspension, dispersion and emulsion, or other forms known for topical application, for example a gel. Where the composition is solid, it is suitably made up into a topically applicable form prior to use, for example by dilution with water to form a paste, lotion or the like. Preferred forms of the composition include lotions, creams, roll-on formulations, sticks, mousses, aerosol and non-aerosol sprays and fabric (e.g. non-woven textile)-applied formulations.

The composition of the invention may be any substance applied to a human body for improving skin properties including one or more of anti-ageing effect, reduced wrinkles, other aspects of skin appearance, cleansing, odour control or general aesthetics. Non-limiting examples of suitable compositions include leave-on skin lotions and creams, shower gels, toilet bars, antiperspirants, deodorants, dental products, shave creams, depilatories, lipsticks, foundations, mascara, sunless tanners and sunscreen lotions.

The cosmetically acceptable carrier may be any known such carriers employed alone or in combination with other carriers. Amounts of the carrier may range from 1 to 99.9%, preferably from 70 to 95%, optimally from 80 to 90% by weight of the composition. Among the useful carriers are water, emollients, fatty acids, fatty alcohols, thickeners and combinations thereof. The carrier may be aqueous, anhydrous or an emulsion. Preferably the compositions are aqueous, especially water and oil emulsions of the W/O or O/W or triplex W/O/W variety. Water when present may be in amounts ranging from 5 to 95%, preferably from 20 to 70%, optimally from 35 to 60% by weight of the composition.

Emollient materials may serve as cosmetically acceptable carriers. These may be in the form of silicone oils, natural or synthetic esters and hydrocarbons. Amounts of the emollients may range anywhere from 0.1 to 95%, preferably between 1 and 50% by weight of the composition.

Silicone oils may be divided into the volatile and non-volatile variety. The term "volatile" as used herein refers to those materials which have a measurable vapour pressure at ambient temperature. Volatile silicone oils are preferably chosen from cyclic (cyclomethicone) or linear polydimethylsiloxanes containing from 3 to 9, preferably from 4 to 5, silicon atoms.

Non-volatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from $5 \times 10^{-6}$ to 0.1 m2/s at 25° C. Among the preferred non-volatile emollients useful in the present compositions are the polydimethyl siloxanes having viscosities from $1 \times 10^{-5}$ to $4 \times 10^{-4}$ m2/s at 25° C.

Another class of non-volatile silicones are emulsifying and non-emulsifying silicone elastomers. Representative of this category is dimethicone/vinyl dimethicone crosspolymer available as Dow Corning 9040, General Electric SFE 839, and Shin-Etsu KSG-18. Silicone waxes such as Silwax WS-L (dimethicone copolyol laurate) may also be useful.

Suitable ester emollients include:
a) Alkyl esters of saturated fatty acids having 10 to 24 carbon atoms. Examples thereof include behenyl neopentanoate, isononyl isonanonoate, isopropyl myristate and octyl stearate.
b) Ether-esters such as fatty acid esters of ethoxylated saturated fatty alcohols.
c) Polyhydric alcohol esters such as ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory. Particularly useful are pentaerythritol, trimethylolpropane and neopentyl glycol esters of C1-C30 alcohols.
d) Wax esters such as beeswax, spermaceti wax and tribehenin wax.
e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean, oil, olive oil, safflower oil, shea butter, jojoba oil and combinations thereof. Animal derived emollients are represented by lanolin oil and lanolin derivatives. Amounts of the natural esters may range from 0.1 to 20% by weight of the compositions.

Hydrocarbons which are suitable cosmetically acceptable carriers include petrolatum, mineral oil, C11-C13 isoparaffins, polybutenes, and especially isohexadecane, available commercially as Permethyl 101A from Presperse Inc.

Fatty acids having from 10 to 30 carbon atoms may also be suitable as a cosmetically acceptable carriers. Examples of this category include pelargonic, lauric, myristic, palmitic, stearic, isostearic, oleic, linoleic, linolenic, hydroxystearic and behenic acids.

Fatty alcohols having from 10 to 30 carbon atoms may also be suitable as a cosmetically acceptable carrier. Examples of this category include stearyl alcohol, lauryl alcohol, myristyl alcohol, oeyl alcohol and cetyl alcohol.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Suitable cellulosic derivatives include sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, optimally from 0.01 to 0.5% by weight of the composition.

Adjunct humectants may be employed in the present invention. These are generally polyhydric alcohol-type materials. Typical polyhydric alcohols include glycerol, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of adjunct humectant may range anywhere from 0.5 to 50%, preferably between 1 and 15% by weight of the composition.

Surfactants may also be present in compositions of the present invention. Total concentration of the surfactant when present may range from 0.1 to 90%, preferably from 1 to 40%, optimally from 1 to 20% by weight of the composition, and is highly dependent upon the type of personal care product. The surfactant may be selected from the group consisting of anionic, nonionic, cationic and amphoteric actives. Particularly preferred nonionic surfactants are those with a C10-C20 fatty alcohol or acid hydrophobe condensed with from 2 to 100 moles of ethylene oxide or propylene oxide per mole of hydrophobe; C2-C10 alkyl phenols condensed with from 2 to 20 moles of alkylene oxide; mono- and di-fatty acid esters of ethylene glycol; fatty acid monoglyceride; sorbitan, mono- and di-C8-C20 fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, C8-C20 acyl isethionates, C6-C20 alkyl ether phosphates, C8-C20 sarcosinates, C8-C20 acyl lactylates, sulfoacetates and combinations thereof.

Useful amphoteric surfactants include cocoamidopropyl betaine, C12-C20 trialkyl betaines, sodium lauroamphoacetate, and sodium laurodiamphoacetate.

Sunscreen agents may also be included in compositions of the present invention. Particularly preferred are such materials as ethylhexyl p-methoxycinnamate (Parsol MCX®), avobenzene (Parsol 1789®) and benzophenone-3 (also known as oxybenzone). Inorganic sunscreen actives may be employed such as microfine titanium dioxide and zinc oxide. Amounts of the sunscreen agents when present may generally range from 0.1 to 30%, preferably from 2 to 20%, optimally from 4 to 10% by weight of the composition.

Antiperspirants and deodorant compositions of the present invention ordinarily will contain astringent actives. Examples include aluminum chloride, aluminum chlorhydrex, aluminum-zirconium chlorhydrex glycine, aluminum sulfate, zinc sulfate, zirconium and aluminum chlorohydroglycinate, zirconium hydroxychloride, zirconium and aluminum lactate, zinc phenolsulfonate and combinations thereof. Amounts of the astringents may range anywhere from 0.5 to 50% by weight of the composition.

Preservatives can desirably be incorporated into the personal care compositions of this invention to protect against the growth of potentially harmful microorganisms. Particularly preferred preservatives are phenoxyethanol, methyl paraben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.0001% to 2% by weight of the composition.

Compositions of the present invention may include vitamins. Illustrative vitamins are vitamin A (retinol), vitamin B2, vitamin B3 (niacinamide), vitamin B6, vitamin C, vitamin E, folic acid and biotin. Derivatives of the vitamins may also be employed. For instance, vitamin C derivatives include ascorbyl tetraisopalmitate, magnesium ascorbyl phosphate and ascorbyl glycoside. Derivatives of vitamin E include tocopheryl acetate, tocopheryl palmitate and tocopheryl linoleate. DL-lianthenol and derivatives may also be employed. Total amount of vitamins when present in compositions according to the present invention may range from 0.001 to 10%, preferably from 0.01% to 1%, optimally from 0.1 to 0.5% by weight-of the composition.

An enzyme may be present as desired, for example amylases, oxidases, proteases, lipases and combinations thereof. Particularly preferred is superoxide dismutase, commercially available as Biocell SOD from the Brooks Company, USA.

Skin lightening compounds may be included in the compositions of the invention. Illustrative substances are placental extract, lactic acid, niacinamide, arbutin, kojic acid, ferulic acid, resorcinol and derivatives including 4-substituted resorcinols and combinations thereof. Amounts of these agents may range from 0.1 to 10%, preferably from 0.5 to 2% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, chamomile, liquorice, aloe vera, grape seed, citrus unshui, willow bark, sage, thyme and rosemary.

Further carrier components may be included such as lipoic acid, retinoxytrimethylsilane (available from Clariant Corp. under the Silcare IM-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from 0.000001 to 10%, preferably from 0.0001 to 1% by weight of the composition.

Colorants, opacifiers and abrasives may also be included in compositions of the present invention. Each of these substances may range from 0.05 to 5%, preferably between 0.1 and 3% by weight of the composition.

The compositions of the present invention can also be, optionally, incorporated into an insoluble substrate for application to the skin such as in the form of a treated wipe.

Another aspect this invention is the inclusion of instructions attached to or otherwise associated with the packageing in which the ketone body or composition of the invention is supplied. The instructions indicate to a consumer topical use of the ketone body or composition on skin, hair or oral mucosae. Packageing itself will usually be printed with the instructions but sometimes a separate written insert within the package may serve to provide the instructions. Typical language includes phrases such as "apply a thin layer to the underarm", "apply regularly to hands", "cleanse skin" and "pump a small amount onto the palm of your hand".

Ketone bodies and compositions of the invention are suitable for improving skin properties and especially in providing an anti-ageing effect. By the term "anti-ageing", we mean that the skin may appear less wrinkled (i.e., there is an anti-wrinkling effect on wrinkles and/or fine lines, including a reduction in wrinkle depth) and that the composition may impart one or more further benefits for the skin selected from: reduced dryness; increased firmness; increased elasticity; increased smoothness; clearer skin; fewer spots, pimples and blemishes (including acne); clearer skin; less sensitive skin; and generally healthier skin.

Ketone bodies and compositions of the invention may exhibit the anti-ageing effect by improving skin cell nutrition or for example by increasing collagen synthesis in the skin and compositions of the invention may be used to increase collagen synthesis (as part of, or separately from, the anti-ageing effect); preferably collagen synthesis is increased by at least 10%, more preferably at least 20% such as at least 25% by weight (e.g., as determined based on the weight of collagen synthesised, preferably over a 14 week period).

The skin may include the skin of the whole body, preferably the face, neck and/or hands. The skin may also include scalp skin with benefits for hair (including reduced ageing) and scalp itch or irritation.

The following examples are illustrative embodiments of this invention. All parts, percentages and proportions referred to herein and in the appended claims are by weight unless otherwise illustrated.

Various methods of measurement of characteristics of the skin are known and provide a means of determining by measurement or visually improvements in skin properties. Examples of Such Methods Include:

Measurement of Skin Hydration

Various methods for determining the hydration state of the stratum corneum have been summarized by Fluhr et al., Skin Res Technol 1999; 5:161-170. Briefly, the Corneometer (Courage & Khazaka) measures skin hydration through detection of epidermal capacitance. The probe is made of two finger-type metal plates close to each other, with a measurement depth of approximately 30 mm. The instrument determines the humidity level of the most external cutaneous layers of the stratum corneum. The action principle of the Corneometer® is based on the modification of the electrical capacities of the detector which is designed in the form of a condenser. The surface of the measurement head, in contact with the skin, modifies its electrical capacity according to the humidity level of the skin. An increase in the value measured by the corneometer is indicative of improved skin hydration.

Measurement of Trans Epidermal Water Loss (TEWL)

An analysis of methods to measure TEWL has been performed by Wilson & Maibach, (1989) Transepidermal water loss, A review, In: Cutaneous Investigation in Health and Disease, Noninvasive Methods and Instrumentation (Leveque, J. L., ed.), pp. 113-130, Dekker, New York, N.Y. The cutaneous barrier acts as a regulator in skin water balance. When this is damaged, the water exchange regulation system becomes destabilised. This means that water migrates more easily to the outside environment, increasing Transepidermal Water Loss. The effectiveness of the cutaneous barrier decreases with age. However, if the condition of the cutaneous barrier improves, water loss decreases as the water exchange regulation mechanism recovers its balance. TransEpidermal Water Loss measurements can be performed with a Servomed "Evaporimeter" EP-3®. A probe made up of two captors is traversed by a flow of water vapour. The difference of the partial pressure is measured between the two captors. This value corresponds to the evaporation speed of a volatile substance (in this case, water). A reduction in TEWL is indicative of improved skin barrier properties Measurement of Skin Elasticity & Firmness Measurements for skin elasticity and firmness are made with a cutometer and described in Escoffier et al, J Invest Dermatol, 93(3):353-7. The measurement is done with an instrument which, using the vacuum principle, sucks up a defined area of skin surface and records it optically. Analysis of the recorded measurement curves makes it possible to determine the elastic and plastic characteristics of the skin. Young skin shows a high degree of elasticity and loses shape only gradually while regaining its original state after the end of the suction procedure. Skin which is young, healthy, supple and adequately moist will have a higher elasticity than an aged dry, rough skin. The cutometer therefore gives a set of measurements which allows us to quantify elastic characteristics. The technique consists of skin aspiration by a measurement probe. The skin is sucked into the orifice of the probe by negative pressure created within the device. The depth to which the skin penetrates into the probe is measured by a non-contact optical measurement system. This system consists of a light source and light receptor, as well as two prisms facing each other, which project the light from transmitter to receptor. Light intensity varies with penetration depth of the skin. The resistance of the skin to be sucked up gives an indication of the firmness of the skin and the ability to return to its original position gives an indication of the elasticity of the skin. A curve is displayed at the end of each measurement which allows several calculations to be made corresponding to skin mechanical properties.

Analysis of Fine Lines, Wrinkles & Skin Smoothness

Skin roughness and wrinkling can be assessed using replicas and skin profilometry as described by Cook, J Soc Cosmet Chem, 1980; 31:339-359. A silicon rubber material such as Silflo is prepared and applied to the test area. Once set it is removed and analysed using optical profilometry. With this measurement method, a parallel stripe pattern is projected onto the skin surface and depicted on the CCD chip of a camera. The 3D measurement effect is achieved by the fact that minute evaluation differences on the skin surface deflect the parallel projection stripes and that these deflections constitute a qualitative and quantitative measurement of the skin profile. The skin profiles are recorded by the CCD camera, digitised, and transferred to the measurement and evaluation computer for qualitative evaluation.

EXAMPLE 1

Composition of the Invention

A composition of the present invention in the form of a cosmetic lotion for topical use is outlined in Table I.

TABLE I

| INGREDIENT | WEIGHT % |
| --- | --- |
| PHASE A | |
| Water | Balance |
| Disodium EDTA | 0.05 |
| Methyl paraben | 0.15 |
| Magnesium aluminum silicate | 0.60 |
| Triethanolamine | 1.20 |
| a D-betahydroxybutyrate butanediol monoester | 1.00 |

TABLE I-continued

| INGREDIENT | WEIGHT % |
|---|---|
| PHASE B | |
| Xanthan gum | 0.20 |
| Natrosol ® 250HHR (ethyl cellulose) | 0.50 |
| Butylene glycol | 3.00 |
| Glycerin | 2.00 |
| PHASE C | |
| Sodium stearoyl lactylate | 0.10 |
| Glycerol monostearate | 1.50 |
| Stearyl alcohol | 1.50 |
| Isostearyl palmitate | 3.00 |
| Silicone fluid | 1.00 |
| Cholesterol | 0.25 |
| Sorbitan stearate | 1.00 |
| Butylated hydroxy toluene | 0.05 |
| Vitamin E acetate | 0.01 |
| PEG-100 stearate | 2.00 |
| Stearic acid | 3.00 |
| Propyl paraben | 0.10 |
| Parsol MCX ® | 2.00 |
| Caprylic/capric triglyceride | 0.50 |
| Hydroxycaprylic acid | 0.01 |
| C12-15 alkyl octanoate | 3.00 |
| PHASE D | |
| Vitamin A palmitate | 0.10 |
| Bisabolol | 0.01 |
| Vitamin A acetate | 0.01 |
| Fragrance | 0.03 |
| Retinol SOC | 0.02 |
| Conjugated linoleic acid | 0.50 |

The composition is suitably prepared by adding the phases in sequence and homogenising the mixture.

EXAMPLE 2

A composition of the present invention in the form of a skin cream for topical use is shown in Table II.

TABLE II

| INGREDIENT | WEIGHT % |
|---|---|
| Glycerin | 6.93 |
| Niacinamide | 5.00 |
| D-betahydroxybutyrate butanediol monoester | 5.00 |
| Permethyl ™ 101A1 | 3.00 |
| Sepigel ™ 3052 | 2.50 |
| Q2-14033 | 2.00 |
| Linseed oil | 1.33 |
| Arlatone ™ 21214 | 1.00 |
| Cetyl alcohol CO-1695 | 0.72 |
| SEFA cottonate5 | 0.67 |
| Tocopherol acetate | 0.50 |
| Panthenol | 0.50 |
| Stearyl alcohol | 0.48 |
| Titanium dioxide | 0.40 |
| Disodium EDTA | 0.10 |
| Glydant ™ Plus6 | 0.10 |
| PEG-100 stearate | 0.10 |
| Stearic acid | 0.10 |
| Purified water | Balance |

1 Isohexadecane (Presperse Inc., South Plainfield, NJ);
3 Polyacrylamide (and) C13-14 isoparaffin(and) laureth-7 (Seppic Corporation, Fairfield, NJ);
3 Dimethicone (and) dimethiconol (Dow Corning Corp. Midland, MI);
4 Sorbitan monostearate and sucrococoate (ICI Americas Inc., Wilmington, DE);
5 Sucrose ester of fatty acid;
6 DMDM Hydantoin (and) iodopropynyl butylcarbamate (Lonza Inc., Fairlawn, NJ).

EXAMPLE 3

A cosmetic composition of the present invention for topical use is shown in Table III.

TABLE III

| INGREDIENT | WEIGHT % |
|---|---|
| Polysilicone-11 | 29 |
| Cyclomethicone | 59 |
| Petrolatum | 11 |
| a D-betahydroxybutyrate butanediol monoester. | 0.2 |
| Dimethicone copolyol | 0.5 |
| Sunflowerseed oil | 0.3 |

EXAMPLE 4

A disposable, single use personal care towelette product is described according to the present invention. A 70/30 polyester/rayon non-woven towelette is prepared with a weight of 1.8 grams and dimensions of 15 cm by 20 cm. Onto this towelette is impregnated a composition with a hydroxybutyrate ester as shown in Table IV below.

TABLE IV

| INGREDIENT | WEIGHT % |
|---|---|
| D-betahydroxybutyrate butanediol monoester | 7.50 |
| Glycerin | 2.00 |
| Hexylene glycol | 2.00 |
| Disodium capryl amphodiacetate | 1.00 |
| Gluconolactone | 0.90 |
| Silicone microemulsion | 0.85 |
| Witch hazel | 0.50 |
| PEG-40 hydrogenated-castor oil | 0.50 |
| Fragrance | 0.20 |
| Vitamin E acetate | 0.001 |
| Water | Balance |

EXAMPLE 5

D-betahydroxybutyrate butanediol monoester was used neat in this experiment. The hands of the user were visually inspected prior to application of the D-betahydroxybutyrate butanediol monoester. The hands had a dry appearance and feel. D-betahydroxybutyrate butanediol monoester was applied to the hands and massaged in to the skin thoroughly. The hands were inspected visually again after 30 minutes and were observed to have a visually noticeable improvement in properties including less dryness, less wrinkling and an improved feel.

EXAMPLE 6

In this example, the effects of R-3-hydroxybutyl-(R)-3-hydroxybutyrate on human dermal fibroblast growth were assessed.

Primary human dermal fibroblasts (HDF), with a seeding capacity of 2,500 cells/cm$^2$, from TCS Cellworks were grown in 96-well plates for 24, 48 and 72 hours in either human fibroblast (HF) basal medium (TCS Cellworks) or basal medium containing 4 mM of the ketone ester, deltaG. The basal medium was changed daily.

Cell viability was determined using a live and dead assay kit, with two colour fluorescence staining of live and dead cells using the probes, Calcein AM and EthD-III. After 10 days incubation, the numbers of live cells was significantly greater when grown in the presence of R-3-hydroxybutyl-(R)-3-hydroxybutyrate (89% vs. 75%, P<0.05) with fewer dead cells. The results are shown in FIG. 1. It can be concluded that the ketone ester according to the invention decreased human dermal fibroblast death.

EXAMPLE 7

Figure 2:
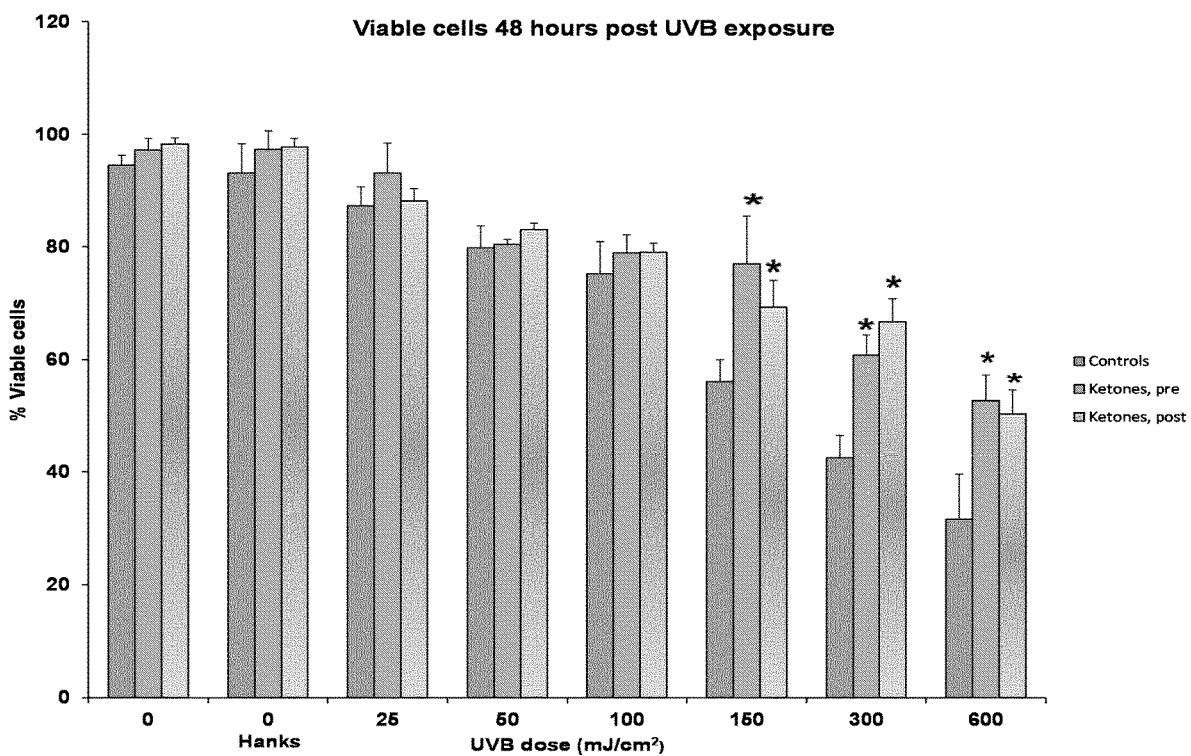
FIG. 2 is a graph depicting the effect of UV radiation on cell survival of human dermal fibroblasts that were pre-incubated or after-treated with R-3-hydroxybutyl-(R)-3-hydroxybutyrate.

Human dermal fibroblast cells were cultured in basal medium in 6-well plates at 50,000 cells per well. The cells were incubated in medium alone or with added 4 mM R-3-hydroxybutyl-(R)-3-hydroxybutyrate. After reaching 80-90% confluence, cells were washed with phosphate-buffered saline and the medium was replaced with a thin layer of Hanks buffer, (a balanced salt solution designed to use with cells in non-$CO_2$ atmospheric conditions). Cells were irradiated at doses of 25, 50, 100, 150, 300 and 600 mJ/$cm^2$ using a portable UVB source (302 nm) with a fluence rate of 0.9 mW/$cm^2$ at cell level. UV irradiation was performed in a fume hood to maintain sterility. After irradiation, cells were washed and incubated in medium alone or with added 4 mM R-3-hydroxybutyl-(R)-3-hydroxybutyrate (as they had been before irradiation). Another group of irradiated cells, which had initially been grown in basal medium without deltaG, was incubated with added 4 mM R-3-hydroxybutyl-(R)-3-hydroxybutyrate. Cell survival was determined by counting viable cells using Trypan blue exclusion at 48 hours after irradiation. The results are shown in FIG. 2

It was found that R-3-hydroxybutyl-(R)-3-hydroxybutyrate protected human dermal fibroblasts from UVB radiation (p<0.05) at doses between 150 and 600 mJ/$cm^2$ when given to the cells after radiation. Providing R-3-hydroxybutyl-(R)-3-hydroxybutyrate both before and after radiation exposure conferred no further benefit.

In summary, R-3-hydroxybutyl-(R)-3-hydroxybutyrate both increased human dermal fibroblast viability and protected dermal fibroblasts from UV damage.

The invention claimed is:

1. A method of maintaining or improving the properties of skin or achieving an anti-aging effect, comprising applying topically to the skin a ketone body which is metabolisable in skin cells comprising (R)-3-hydroxybutyrate butanediol monoester or (R)-3-hydroxybutyl-(R')-hydroxybutyrate to a subject in need thereof, wherein maintaining or improving the properties of skin or achieving an anti-aging effect comprise protecting against the effects of ultra violet (UV) radiation.

2. A method of protecting skin or reducing the deterioration of skin due to the effects of UV radiation, comprising applying topically to the skin a ketone body which is metabolisable in skin cells comprising (R)-3-hydroxybutyrate butanediol monoester or (R)-3-hydroxybutyl-(R')-hydroxybutyrate to a subject in need thereof.

3. The method of claim 2, wherein the ketone body further comprises an oligomer of hydroxybutyrate, triolide, acetoacetate and esters thereof, or acetoacetyl oligomers.

4. The method of claim 2, wherein the ketone body further comprises enantiomerically enriched R-3-hydroxybutyl-(R)-3-hydroxybutyrate.

5. A method for protecting skin or reducing the deterioration of the skin due to the effects of UV radiation, comprising applying topically to the skin a composition which is metabolisable in skin cells comprising (R)-3-hydroxybutyrate butanediol monoester or (R)-3-hydroxybutyl-(R')-hydroxybutyrate and an excipient to a subject in need thereof, wherein the composition is an emulsion having an aqueous phase in an oil phase (W/O type), an oil phase in an aqueous phase (O/W type), or an aqueous phase in an oil phase in an aqueous phase (W/O/W type).

6. The method of claim 5, wherein the excipient comprises a cosmetically acceptable carrier.

7. The method of claim 5, wherein the deterioration of skin is due to aging or due to the harmful effects of radiation.

8. The method of claim 5, wherein the level of ketone body comprises at least 1% by weight of the composition.

9. The method of claim 5, wherein the excipient comprises polyethylene glycol.

* * * * *